United States Patent [19]
Beiter et al.

[11] 4,153,574
[45] May 8, 1979

[54] STABLE DISPERSIONS CONTAINING TRIORGANOTIN FLUORIDES

[75] Inventors: Charles B. Beiter, Carteret; Leroy A. Hafner, Edison, both of N.J.

[73] Assignee: M&T Chemicals Inc., Stamford, Conn.

[21] Appl. No.: 763,406

[22] Filed: Jan. 28, 1977

[51] Int. Cl.² ............................................. B01J 13/00
[52] U.S. Cl. ................... 252/316; 106/15.05; 424/288
[58] Field of Search ...................... 252/316; 106/15 R; 424/288

[56] References Cited

U.S. PATENT DOCUMENTS

| | | | |
|---|---|---|---|
| 3,789,057 | 1/1974 | Reifenberg et al. | 424/288 X |
| 3,801,534 | 4/1974 | Beers | 260/37 EP |
| 4,012,503 | 3/1977 | Freiman | 106/15 R X |

FOREIGN PATENT DOCUMENTS 1279857  6/1972  United Kingdom.

Primary Examiner—Benjamin R. Padgett
Assistant Examiner—E. Suzanne Parr
Attorney, Agent, or Firm—Kenneth G. Wheeless; Robert Spector

[57] ABSTRACT

The tendency of dispersions containing triorganotin fluorides in organic liquids to agglomerate is avoided by using as the dispersion medium specified organic liquids in combination with from 0.5 to 10% based on the weight of the dispersion, of specified inorganic compounds. The choice of both organic liquid and inorganic compound is critical to achieving long-term stability of the resultant dispersion.

7 Claims, No Drawings

STABLE DISPERSIONS CONTAINING TRIORGANOTIN FLUORIDES

FIELD OF THE INVENTION

This invention relates to compositions containing a dispersed form of a triorganotin fluoride. More particularly, this invention relates to stable dispersions of triorganotin fluorides which are capable of being stored for extended periods of time without any significant increase in viscosity.

A number of triorganotin fluorides, including tri-n-butyltin fluoride, effectively inhibit the attachment and growth of barnacles and other organisms responsible for fouling of submerged surfaces such as the hulls of sea-going vessels and the pilings of docks and other facilities exposed to salt water. The triorganotin fluorides are, therefore, useful as the toxicant for antifouling coatings. A typical antifouling coating contains the toxicant, one or more pigments and a film-forming polymer. All of these components are dissolved or dispersed in an organic solvent such as xylene or toluene, optionally in combination with a ketone such as 2-butanone.

Up until now, acceptable coatings containing triorganotin fluorides, which are solid materials at ambient temperatures, have been difficult to prepare. Dispersions of triorganotin fluorides in organic solvents exhibit a strong tendency to agglomerate in the form of large particles. These materials therefore cannot be dispersed in coating compositions or organic solvents by mixing at high speeds. This unusual behavior has been explained in terms of a difference between the electronegativities of tin and fluorine. This difference causes a relatively weak attractive force between the tin atom on one molecule and the fluorine atom on an adjacent molecule, resulting in a structure resembling that of a linear polymer molecule. Regardless of the cause, the agglomeration is undesirable, since it makes it difficult or impossible to prepare a useful coating formulation wherein the maximum particle size is 45 microns or less. This degree of fineness cannot be achieved without tedious, time-consuming grinding using a pebble mill or a ball mill. Even following such a grinding procedure, there may be a number of hard agglomerates still present in the formulation. These agglomerates must be removed to obtain a useful coating composition.

It is, therefore, an objective of this invention to obtain stable disperions of triorganotin fluorides which can be readily dispersed in coating compositions without the need for grinding to achieve the desired particle size.

Surprisingly, it has now been found that triorganotin fluorides such as tri-n-butyltin fluoride can be dispersed in organic solvents without agglomeration to yield stable compositions, if the dispersion is prepared in the presence of certain inorganic compounds as disclosed in the following specification. The resultant compositions remain stable for extended periods of time and can readily be incorporated into coating compositions, including paints.

Japanese Patent Publication No. 7338847 discloses heating tri-n-butyltin fluoride at 40° to 60° C. in a liquid hydrocarbon or halogenated hydrocarbon that boils from 50° to 200° C. The resultant slurry hardens upon standing for any appreciable length of time, and hence is not practical for incorporation into antifouling coatings. Even after being ground the resultant particles do not yield a dispersion of adequate "fineness".

SUMMARY OF THE INVENTION

This invention provides a stable, thixotropic dispersion of a triorganotin fluoride, said dispersion consisting essentially of:

(1) from 40 to 70% by weight of a triorganotin fluoride of the formula $R_3SnF$, wherein R is alkyl containing from 2 to 12 carbon atoms or phenyl;

(2) from 20 to 60% by weight of an organic liquid medium selected from the group consisting of alcohols containing from 4 to 12 carbon atoms, aliphatic hydrocarbons containing from 5 to 12 carbon atoms and aromatic hydrocarbons having a kauri butanol value of 96 or less;

(3) from 0.5 to 10% by weight of a compound selected from the group consisting of:
  (a) carbonic, phosphoric, hyphosphorous and phosphorous acid salts of lithium, sodium, beryllium, magnesium and calcium,
  (b) carboxylic acid salts of lithium, sodium, beryllium, magnesium and calcium, wherein said carboxylic acid contains from 2 to 12 carbon atoms, and
  (c) hydroxides of lithium, sodium, potassium, beryllium, magnesium and calcium.

DETAILED DESCRIPTION OF THE INVENTION

The novel feature of the present triorganotin fluoride compositions resides in the presence of certain inorganic compounds. These compounds stabilize the dispersion by preventing agglomeration of the triorganotin fluoride particles. The accompanying examples demonstrate that all inorganic compounds are not suitable stabilizers, and it is difficult to predict without experimentation which compounds are operable. For example, while sodium compounds are generally useful, the only effective potassium compound is the hydroxide.

The cationic portion of those compounds found to be effective dispersion stabilizers is derived from an alkali metal (lithium and sodium) or an alkaline earth metal (beryllium, calcium and magnesium). The anionic portion of the molecule is a residue of an inorganic acid (carbonic or a phosphorus-containing acid) or a carboxylic acid containing from 2 to 12 carbon atoms. Representative carboxylic acids include acetic, propionic, butyric, hexoic, heptanoic, cyclohexanecarboxylic and benzoic acids.

By comparison, a dispersion containing sodium chloride solidifies upon standing. This is also true for dispersions containing the potassium analogs of the aforementioned sodium compounds with the exception of potassium hydroxide, which, surprisingly, yields a stable dispersion.

In addition to choice of the proper inorganic compound, choice of the organic liquid is also critical to obtaining a stable dispersion of a triorganotin fluoride. Suitable organic liquids include aliphatic hydrocarbons and aromatic hydrocarbons having a kauri butanol value of 96 or less. The kauri butanol value of a hydrocarbon solvent is equal to the volume in cubic centimeters (measured to 25° C.) of a given solvent that will produce a specified degree of turbidity when added to 20 g. of a standard solution of kauri resin in normal butanol. Toluene has a value of 105. The test method is published by the American Society for Testing and Materials as ASTM Test No. 01133-61 (reapproved in 1973). The pertinent portions of this testing procedure are hereby incorporated by reference.

Representative useful liquid hydrocarbons include aliphatic hydrocarbons. These hydrocarbons can be used individually or in mixtures that are commercially available as mineral spirits, petroleum ether and naphtha. The class of aromatic hydrocarbons includes xylene. Toluene has a kauri butanol value of greater than 96 and is therefore not a suitable medium for the present dispersions. Other useful liquid media include alcohols containing 1, 2 or 4 carbon atoms, such as methanol, ethanol and butanol. Surprisingly, a stable dispersion cannot be prepared in n-propanol.

The triorganotin fluorides that can be employed in the stable dispersions of the invention are of the general formula $R_3SnF$, wherein R is alkyl containing from 2 to 12 carbon atoms or phenyl. If the dispersion is to be incorporated into a coating material intended to inhibit fouling by barnacles and other organisms on ship hulls and other normally submerged structures, R contains from 3 to 6 carbon atoms and is preferably n-butyl or phenyl.

Using the inorganic compounds and organic liquids disclosed in the preceding specifications and accompanying claims as being suitable stabilizers and liquid media for the present dispersions, it is possible to prepare compositions containing from about 10% by weight or less up to about 70% of a triorganotin fluoride. It has heretofore not been possible to incorporate more than about 40% by weight of a triorganotin fluoride in a dispersion. The maximum amount of fluoride that can be incorporated into a useful dispersion will, of course, vary somewhat depending upon the particular inorganic compound and organic liquid.

The physical form of the present dispersions may vary from a viscous liquid to a semi-solid paste, depending upon the concentration of triorganotin fluoride. One important advantage of these compositions is that they can be easily blended with other ingredients conventionally present in paints and other coating compositions. These additional ingredients may include film-forming natural or synthetic polymers such as rosin and copolymers of vinyl chloride with one or more ethylenically unsaturated monomers, pigments such as titanium dioxide and iron oxide, dispersing aids, particularly clays such as bentonite, and one or more organic solvents.

Incorporating solid triorganotin fluorides in paint formulations is a lengthy, time-consuming procedure due to the tendency of the fluoride to agglomerate. The resultant paint usually requires several hours of grinding to obtain a fineness of 4 to 5 on the Hegman N.S. Scale of 0 (no grind) to 10 (excellent grind). A rating of 4 to 5 on this scale is equivalent to an average particle size of from 40 to 70 microns. Similar problems resulting from agglomeration are encountered if an attempt is made to disperse the triorganotin fluoride in an organic solvent prior to incorporating it into a paint formulation. In addition, once a dispersion of the desired particle size is obtained, it rapidly hardens to a waxy solid and therefore cannot be stored for any appreciable period of time.

The accompanying examples disclose preferred embodiments of the present compositions and should not be interpreted as limiting the scope of the accompanying claims. In the examples all parts and percentages are by weight unless otherwise indicated.

EXAMPLE 1

Dispersions of tri-n-butyltin fluoride were prepared by blending 60 parts of this compound, 5 parts of the inorganic stabilizer and 35 parts of a mixture containing 64% special naphthalite (a mixture of liquid hydrocarbons containing less than 8% of aromatic hydrocarbons), 12% ethyl benzene, 9% n-butyl acetate, 5% isobutyl acetate and 10% n-butanol. The flash point of the mixture is 14.4° C., the kauri butanol number is 36 and the boiling range is from 123° to 145° C. One hundred grams of the resultant mixture were placed in a cylindrical container measuring two inches (5.1 cm.) in diameter and 4.5 inches (11.4 cm.) in height. Into the same container were also placed 250 grams of stainless steel spheres measuring 4.7 millimeters in diameter. The container was then sealed and shaken vigorously for twenty minutes, after which the contents of the container were emptied onto a large mesh wire screen. Dispersions which solidified during milling and crumbled when prodded with a spatula were considered unacceptable and were not tested further. Acceptable materials were either viscous liquids or homogeneous, coherent semi-solids which could be forced through the openings of the screen using a spatula. Those materials which passed through the screen were collected and maintained under ambient conditions for two days. At the end of the period, they were examined to determine whether any changes in their physical form had occurred during this interval. Those materials which had solidified and could no longer be stirred with a spatula were considered unacceptable. All of the acceptable materials were thixotropic semi-solids or viscous liquids that exhibited a significant viscosity reduction under shear. Some of the materials appeared to be coherent solids yet could readily be stirred by hand with a spatula using only a minimal amount of force.

Inorganic compounds yielding acceptable dispersions included:
Lithium Acetate
Sodium Carbonate
Sodium Bicarbonate
Sodium Hypophosphite (as the monohydrate)
Sodium Hydrogen Phosphite (as the pentahydrate)
Sodium Phosphate
Sodium Hydrogen Phosphate (as the anhydrous salt)
Sodium Hydroxide
Sodium Silicate
Sodium Acetate
Potassium Hydroxide
Magnesium Bicarbonate
Magnesium Hydrogen Phosphate
Magnesium Hydroxide
Magnesium Acetate
Calcium Carbonate
Calcium Phosphate
Calcium Hydroxide
Calcium Acetate
Calcium Lactate.

Inorganic compounds which did not yield acceptable dispersion included:
Sodium Chloride
Sodium Sulfate
Potassium Carbonate
Potassium Phosphite
Potassium Phosphate
Potassium Chloride
Potassium Sulfate Potassium Acetate
Magnesium Sulfate
Calcium Sulfate.

The data from the evaluation demonstrate that while a number of sodium compounds are acceptable stabilizers, the corresponding potassium compounds, with the exception of the hydroxide, will not prevent solidification of the dispersion. The hydroxides of the other alkali and alkaline earth metals of this invention are also suitable, as were the acetates of lithium, sodium and the elements of groups II A.

It is believed that an effective stabilizer will interfere with the formation of strong bonds between the fluorine atoms on one molecule and tin atoms on adjacent molecules. This bond formation is believed responsible for the agglomeration which almost always occurs when a triorganotin fluoride is dispersed into an organic solvent in the absence of one of the present inorganic compounds.

EXAMPLE 2

The effect of various organic liquids or diluents on the stability of a dispersion containing 60% by weight of tri-n-butyltin fluoride, 5% of calcium carbonate and 35% of the organic liquid was determined by preparing a dispersion as described in the preceding example. Those dispersions which could be classified as viscous liquids or coherent semi-solids following the initial milling operation were stored for one week under ambient conditions and then examined to determine whether the original thixotropic character had been retained.

The organic liquids evaluated included a mixture of aromatic hydrocarbons available as Solvesso® 150 from the Exxon Company and typically having a flash point from 145° to 150° F. (63° to 65° C.), VM&P naphtha [a mixture of aliphatic hydrocarbons typically having a flash point of 6.7° C. (tag closed cup) and a boiling range from 118° to 139° C.]; mineral spirits [a mixture of aliphatic hydrocarbons typically having a flash point of 42.2° C. (tag closed cup) and a boiling range from 160° to 196° C.]; ethyl benzene, amyl acetate, a mixture (A) containing 33.3% of VM&P naphtha, 28.9% cyclohexane and 37.8% amyl acetate and a second mixture (B) containing 34.2% mineral spirits, 4.4% Solvesso® 150, 12.2% ethyl benzene and 49.2% amyl acetate.

Also included in the evaluation were cyclohexane, xylene, methyl ethyl ketone, n-butyl acetate, isobutyl acetate, n-butanol, ethylene glycol, n-propanol, octanol, Cellosolve® acetate (ethylene glycol monomethyl ether monoacetate) and toluene. Of the solvents evaluated, the two mixtures (A&B), VM&P naphtha, Solvesso® 150, mineral spirits, xylene, n-butanol and octanol produced acceptable dispersions. Dispersions prepared using the other solvents hardened during the one week storage period or were too stiff and gum-like for use in a paint formulation.

EXAMPLE 3

Dispersions containing 60% by weight of tri-n-butyltin fluoride (TBTF) prepared as described in the preceding Example 1 using calcium carbonate as the stabilizer, were incorporated with a conventional paint formulation of the following composition:

| | Parts |
| --- | --- |
| Titanium dioxide | 15.12 |
| Talc (Magnesium Silicate) | 11.22 |

-continued

| | Parts |
| --- | --- |
| Zinc Oxide | 7.08 |
| Vinyl Resin (VAGH) | 11.16 |
| Rosin | 3.73 |
| Methyl Ethyl Ketone | 20.31 |
| Xylene | 18.84 |
| Bentonite | 0.51 |
| Methanol (95%) | 0.15 |
| TBTF Dispersion | As Required |

The solvent employed to prepare the dispersions was a mixture containing 64% special naphthalite, 12% ethyl benzene, 9% n-butyl acetate, 5% isobutyl acetate and 10% n-butanol. Special naphthalite is described in the preceding Example 1.

The amount of tri-n-butyltin fluoride dispersion employed was equivalent to 12% by weight of the compound in the formulation. The dispersion was blended together with the other components of the formulation to achieve a homogeneous mixture.

The paint was evaluated using a Hegman N.S. gauge to determine "fineness" of the grind. A 0.003 inch (0.0076 cm.)-thick film was applied to a metal surface using a draw-down blade and the texture of the resultant film was evaluated using the following scale:

1. Rough surface easily detected by rubbing a hand over the surface of the coating
2. 10-20 observable lumps uniformly distributed on paint surface
3. Several lumps visible
4. Smooth The results of the paint evaluations are recorded in the following table. A Hegman fineness of 4 or 5 is considered acceptable:

| % CaCO$_3$ | Hegman Grind No. | Film Rating |
| --- | --- | --- |
| 10 | — | 4 |
| 5 | — | 4 |
| 2.5 | 4 | 4 |
| 1 | 4-5 | 3-4 |
| 0.5 | 4-5 | 1-2 |

The film prepared using a dispersion containing 0.5% by weight of calcium carbonate and 60% tri-n-butyltin fluoride was too rough in texture to be considered acceptable, however this level of calcium carbonate would be sufficient to stabilize dispersions containing less than 60% of the triorganotin compound, for example about 50% by weight.

What is claimed is:

1. A stable thixotropic dispersion, said dispersion consisting essentially of:
    (a) from 40 to 70% by weight of a triorganotin fluoride of the formula $R_3SnF$ wherein R is alkyl containing from 2 to 12 carbon atoms or phenyl;
    (b) from 20 to 60% by weight of an organic liquid selected from the group consisting of alcohols containing from 4 to 12 carbon atoms, aliphatic hydrocarbons containing from 5 to 12 carbon atoms and aromatic hydrocarbons having a kauri butanol value of 96 or less;
    (c) from 0.5 to 10% by weight of a compound selected from the group consisting of:
        (1) carbonic, phosphoric, hypophophorous and phosphorous acid salts of lithium, sodium, beryllium, magnesium and calcium, (2) carboxylic acid salts of lithium, sodium, beryllium, magnesium and calcium, wherein said carboxylic acid contains from 2 to 12 carbon atoms, and (3) hydroxides of lithium, sodium, potassium, beryllium, magnesium and calcium.

2. A stable dispersion as set forth in claim 1 wherein R contains from 3 to 6 carbon atoms.

3. A stable composition as set forth in claim 2 wherein R is butyl.

4. A stable dispersion as set forth in claim 1 wherein said liquid organic medium is a mixture containing two aliphatic hydrocarbons.

5. A stable dispersion as set forth in claim 1 wherein said organic liquid is xylene.

6. A stable dispersion as set forth in claim 1 wherein said compound is selected from the group consisting of lithium acetate, sodium carbonate, sodium bicarbonate, sodium hypophosphite, sodium hydrogen phosphite, sodium phosphate, sodium hydrogen phosphate, sodium hydroxide, sodium silicate, sodium acetate, potassium hydroxide, magnesium bicarbonate, magnesium hydrogen phosphate, magnesium hydroxide, magnesium acetate, calcium carbonate, calcium phosphate, calcium hydroxide, calcium acetate and calcium lactate.

7. A stable dispersion as set forth in claim 1 wherein said organic liquid contains from 5 to 49.2% by weight of an acetic acid ester wherein the alcohol residue of said ester contains 4 or 5 carbon atoms.

* * * * *